(12) United States Patent
Jones et al.

(10) Patent No.: US 9,149,665 B2
(45) Date of Patent: *Oct. 6, 2015

(54) METHOD AND COMPOSITION FOR REDUCING APPEARANCE OF WRINKLES

(75) Inventors: Brian C. Jones, Flower Mound, TX (US); Michelle D. Hines, Hickory Creek, TX (US)

(73) Assignee: Avon Products, Inc., New York, NY (US)

( * ) Notice: Subject to any disclaimer, the term of this patent is extended or adjusted under 35 U.S.C. 154(b) by 16 days.

This patent is subject to a terminal disclaimer.

(21) Appl. No.: 11/789,017

(22) Filed: Apr. 23, 2007

(65) Prior Publication Data

US 2007/0292537 A1 Dec. 20, 2007

Related U.S. Application Data

(63) Continuation of application No. PCT/US2005/046190, filed on Dec. 20, 2005.

(60) Provisional application No. 60/638,147, filed on Dec. 22, 2004.

(51) Int. Cl.
| | |
|---|---|
| *A61K 8/63* | (2006.01) |
| *A61Q 19/08* | (2006.01) |
| *A61K 8/64* | (2006.01) |
| *A61K 8/97* | (2006.01) |

(52) U.S. Cl.
CPC . *A61Q 19/08* (2013.01); *A61K 8/63* (2013.01); *A61K 8/64* (2013.01); *A61K 8/97* (2013.01); *A61K 2800/782* (2013.01)

(58) Field of Classification Search
None
See application file for complete search history.

(56) References Cited

U.S. PATENT DOCUMENTS

| | | | |
|---|---|---|---|
| 4,985,459 A | | 1/1991 | Sunshine et al. |
| 5,560,917 A | * | 10/1996 | Cohen et al. ................ 424/401 |
| 5,824,312 A | | 10/1998 | Unger et al. |
| 5,869,060 A | | 2/1999 | Yoon et al. |
| 6,153,208 A | | 11/2000 | McAtee et al. |
| 6,338,855 B1 | | 1/2002 | Albacarys et al. |
| 6,344,461 B1 | | 2/2002 | Breton et al. |
| 6,348,200 B1 | | 2/2002 | Nakajima et al. |
| 6,866,856 B2 | * | 3/2005 | Lu et al. ................... 424/401 |
| 7,060,303 B2 | * | 6/2006 | Jones ........................ 424/725 |
| 2002/0081291 A1 | | 6/2002 | Hawrot |
| 2002/0192245 A1 | | 12/2002 | Jensen et al. |
| 2004/0013618 A1 | * | 1/2004 | Passi ........................ 424/59 |
| 2004/0067245 A1 | | 4/2004 | Ptchelintsev et al. |
| 2004/0115146 A1 | | 6/2004 | Mahalingam et al. |
| 2004/0126352 A1 | * | 7/2004 | Jones ........................ 424/74 |
| 2004/0191208 A1 | * | 9/2004 | Courtin ..................... 424/74 |

FOREIGN PATENT DOCUMENTS

| | | |
|---|---|---|
| JP | 63208531 | 8/1988 |
| JP | 201199871 A | 7/2001 |
| JP | 2001213752 A | 8/2001 |
| JP | 2002121112 A | 4/2002 |
| JP | 2003238441 A | 8/2003 |
| JP | 2004035454 A | 2/2004 |
| KR | 2002016960 A * | 3/2002 |
| WO | 03/057234 A1 | 7/2003 |
| WO | 2004/060285 A2 | 7/2004 |
| WO | 2004/060289 A2 | 7/2004 |
| WO | 2004/100889 A2 | 11/2004 |

OTHER PUBLICATIONS

Michaelson, Daniel M. et al., Mechanishm of acetylcholine release: . . . ; Proc. Natl Acad. Sci USA; vol. 76, No. 12, pp. 6336-6340, Dec. 1979.

Gaudry-Talarmain, et al., Nitric oxide Biology and Peroxynitrite Affect Differently Acetylcholin Release . . . ; Biology and Chemistry, vol. 1, No. 4, Aug. 1997, p. 330-345.

Khan, Wasiuddin A. et al.; Acute Sarin Exprosure Causes Differential Regulation . . . ; Toxicological Sciences, vol. 57, 112-120 (2000).

Atarashii Keshouhin Sozai no Kounou, Kouka, Sayou. 1998. Efficacy, Effects and Actions of New Cosmetic Materials. vol. 1. CMC Publishing Co., Ltd. p. 349-351.

* cited by examiner

*Primary Examiner* — Terry A McKelvey
*Assistant Examiner* — Catherine Chen
(74) *Attorney, Agent, or Firm* — David M. Joyal; Joan M. McGillycuddy

(57) ABSTRACT

The present invention provides a cosmetic composition having a cosmetically acceptable vehicle and one or more gap junction inhibitors and/or one or more choline acetyl transferase (CAT) inhibitors in an amount effective for reducing the appearance of deep wrinkles on the skin. Also provided is a method of reducing the appearance of deep wrinkles on the skin, including the steps of topically applying to the skin the above cosmetic composition in an amount and for a period of time sufficient to reduce the appearance of deep wrinkles on the skin.

8 Claims, No Drawings

US 9,149,665 B2

METHOD AND COMPOSITION FOR REDUCING APPEARANCE OF WRINKLES

This application claims priority as a continuation of International Application Serial No. PCT/US05/46190 filed Dec. 20, 2005, which claims priority as a nonprovisional application to U.S. Provisional Application No. 60/638,147 filed Dec. 22, 2004.

BACKGROUND OF THE INVENTION

1. Field of the Invention

The present invention relates to a cosmetic composition having one or more of a gap junction inhibitor and/or one or more of choline acetyl transferase (CAT) inhibitors. More particularly, the present invention relates to a method of relaxing facial skeletal muscles and reducing the appearance of deep wrinkles.

2. Description of the Related Art

The Purslane plant family includes including *Portulaca oleracea* ("green purslane"), *Portulaca sativa* ("golden purslane"), and *Atriplex portulacoides* ("sea purslane").

The plant *Portulaca oleracea* belongs to a genus of succulent annuals commonly occur in moderate to warm climates and include Purslane, Pigweed, Munyeroo, Thukouro, Lifa, Coupier, Little Hogweed, and Perpine. The juice and aqueous extracts from this plant have been used to treat various illnesses such as swelling, whitlow, bruises, boils, earache, toothache, swelling, abscesses (topical) and as a vermifuge and diuretic (Okwuasaba et al., 1986).

The Golden Purslane (*Portulaca sativa*) is a variety of Purslane with yellow leaves, less hardy than green purslane, but possessing the same qualities. The seeds of an individual plant have been known to produce both green and golden leaves. Other species of Purslane plants include Sea Purslane (*Atriplex portulacoides*), which is commonly found along the sea shores of England and Ireland. A review of the records for folklore and scientific uses of *Portulaca oleracea* indicate that this species has had many medicinal uses, such as, significant anti-inflammatory and analgesic effects (Chan et al., 2000), anti-mutagenicity (Yet et al., 2001), antifungal (Oh et al., 2000), antifertility (Verma et al., 1982), reduced cancer and heart disease (Mohamed et al., 1994), controlling intestinal worms, parasites (Quinlan et al., 2002) as well as for application towards strangury, dry cough, shortness of breath, immoderate thirst, inflammation and sores, hot agues, want of sleep, all pains in the head proceedings from the heat, and the frenzy (Grieve's A Modern Herbal), for the treatment of cancer (U.S. Pat. No. 5,869,060, Yeon et al., issued Feb. 9, 1999), as an anti-microbial and antifungal active (U.S. Pat. No. 6,338,855, Albacarys et al., issued Jan. 15, 2002), and as a non-steroidal cosmetic soothing active (U.S. Pat. No. 6,153,208, McAtee et al., issued Nov. 28, 2000), as a sunscreen agent from natural sources (U.S. Pat. No. 5,824,312, Unger et al., issued Oct. 20, 1998), as an antidiabetic agent to control blood sugar levels (Japanese Patent No. JP 63,208,531, Kin et al., published Aug. 30, 1988) and it has been referenced for the use as cosmetic soothing agents (U.S. Pat. No. 4,985,459, Sunshine et al., issued Jan. 15, 1991).

However, none of these patents disclose the use of *Portulaca oleracea* in the treatment of fine lines and wrinkles. In addition, while the properties of *Portulaca oleracea* as a muscle relaxant have also been studied (Okwuasaba et al., 1986, Okwuasaba et al., 1987(1), Okwuasaba et al., 1987(2), Okwuasaba et al., 1987(3), Parry et al., 1987(1), Parry et al., 1987(2), Parry et al., 1988, Parry et al., 1993, Habtemarin et al., 1993, Radhakrishnan et al., 2001), none of these studies report the use of *Portulaca* for reducing facial lines and wrinkles as directed by this application.

Botulinum toxin (also known by the tradename, Botox™, Allergen, Irvine, Calif.), is currently in vogue for treating wrinkles and fine lines, and acts on states of muscular spasticity by specifically inhibiting neurotransmission in nerve cells, thereby causing contracted muscles to relax (e.g., A. Blitzer et al., 1993; U.S. Pat. No. 6,344,461 B1 to L. Breton et al.). This toxin has been found to act on wrinkles of the glabella (wrinkles between the eyebrows) when injected subcutaneously, (see, J. D. Carruthers, 1992, U.S. Pat. No. 6,344, 461 B1 to L. Breton et al.).

However, the full extent of adverse effects related to long-term use of botulinum toxin and products or treatments containing this material are still not well established. Botulinum toxin treatment has been associated with a number of side effects including, transient fatigue, dysphagia, neck weakness, hoarseness, and localized pain. In addition, many patients who preliminarily respond to botulinum toxin, subsequently become non-responsive to treatment or exhibit muscle recruitment at the treatment site (where paralysis of a set of muscles leads to recruitment of other muscle groups in an attempt to counteract the paralysis, thereby causing wrinkles to actually become more prominent) (see, for instance, Becker, 2002; U.S. Patent No. US2002/00812914 to Hawrot).

Commonly owned U.S. Patent Publication No. 20040126352 A1 describes a composition and a method of improving the aesthetic appearance of skin using a composition having a Purslane plant, including treatment of fine lines and wrinkles.

Safe and effective of compositions to treat, prevent, reduce, inhibit, and/or improve the dermatological signs of aging, would be advantageous for the formulation of treatments and products for the skin. Therefore, there is a need in consumer products and cosmetic industry for a composition and method that can reduce the appearance of deep wrinkles.

As described herein, the present invention provides such a beneficial method and composition effective in the treatment of deep wrinkles.

The present invention is applicable to a variety of personal care products including, but not limited to, skin care and personal care cosmetics.

SUMMARY OF THE INVENTION

It is an object of the present invention to provide a cosmetic composition having one or more gap junction inhibitors and/ or one or more choline acetyl transferase (CAT) inhibitors.

It is another object of the present invention to provide a method of relaxing facial skeletal muscles and reducing the appearance of deep wrinkles.

It is still another object of the present invention to employ choline transacetylation inhibitors, such as, *stenolama chusana, portulaca oleracea, gynostemma pentaphyllum*, and *morinda citrifolia* in topical application of cosmetics and/or cosmeceuticals to relax facial skeletal muscles and reduce the appearance of deep wrinkles through reduced activity of a choline acetyl transferase enzyme.

It is yet another object of the present invention to employ gap junction inhibitors, such as, Gap 27 peptides, glycyrrhetinic acid, an isoform of glycyrrhetinic acid, and any combinations thereof, in topical application of cosmetics and/or cosmeceuticals to relax facial skeletal muscles and reduce the appearance of deep wrinkles through relax facial skeletal muscles.

It is a further object of the present invention to employ both gap junction inhibitors and choline acetyl transferase (CAT) inhibitors in topical application of cosmetics and/or cosmeceuticals to relax facial skeletal muscles and reduce the appearance of deep wrinkles.

It is still a further object of the present invention to employ one or more Gap 27 peptides, glycyrrhetinic acid, an isoform of glycyrrhetinic acid, *stenolama chusana, portulaca oleracea, gynostemma pentaphyllum*, and *morinda citrifolia*, in any combinations, to relax facial skeletal muscles and reduce the appearance of deep wrinkles.

It is yet a further object of the present invention to provide a cosmetic product, such as, a skin care and personal care product that can relax facial skeletal muscles and thereby reduce the appearance of deep wrinkles.

The present invention provides such a cosmetic composition having one or more of a gap junction inhibitors and/or one or more of choline acetyl transferase (CAT) inhibitors.

Accordingly, the present invention provides a cosmetic composition having a cosmetically acceptable vehicle and one or more gap junction inhibitors and/or one or more choline acetyl transferase (CAT) inhibitors according to the present invention in an amount effective for reducing the appearance of deep wrinkles on the skin.

The present invention also provides a method of reducing the appearance of deep wrinkles on the skin. The method includes the steps of topically applying to the skin a cosmetic composition comprising a cosmetically acceptable vehicle; and an effective amount of one or more of a gap junction inhibitors and/or one or more of choline acetyl transferase (CAT) inhibitors in an amount and for a period of time sufficient to reduce the appearance of deep wrinkles on the skin.

These and other objects and advantages of the present invention are achieved by the use of the cosmetic composition according to the present invention in cosmetic and personal care products applications to provide relaxation of facial skeletal muscles and effective reduction in the appearance of deep wrinkles.

DETAILED DESCRIPTION OF THE PREFERRED EMBODIMENTS

The present invention provides a cosmetic composition and a method of using the cosmetic composition to reduce the appearance of deep wrinkles by relaxing the facial skeletal muscles.

The cosmetic composition includes a cosmetically acceptable vehicle; and an effective amount of one or more of a gap junction inhibitors and/or one or more of choline acetyl transferase (CAT) inhibitors.

The present method employs:

(1) choline transacetylation inhibitors through reduced activity of the choline acetyl transferase enzyme, including but not limited to, *stenolama chusana, portulaca oleracea, gynostemma pentaphyllum*, and *morinda citrifolia*, to relax facial skeletal muscles and reduce the appearance of deep wrinkles in topical application of cosmetics and/or cosmeceuticals; and/or (2) gap junction inhibitors, including but not limited to, Gap 27 peptides, glycyrrhetinic acid, an isoforms of glycyrrhetinic acid, and any combinations thereof, to relax facial skeletal muscles and reduce the appearance of deep wrinkles in topical application of cosmetics and/or cosmeceuticals.

GAP 27 peptide is derived from connexin 43, which is a selective gap junction blocker. GAP 27 peptide attenuates in vitro ACh-induced arterial relaxation and reduces $K^+$-mediated smooth muscle repolarisation in endothelium-intact vessels.

GAP 27 peptide has the Formula $C_{60}H_{101}N_{15}O_{17}$ and a M—.W. of 1304.55 with a Peptide Sequence Ser-Arg-Pro-Thr-Glu-Lys-Thr-Ile-Phe-Ile-Ile (SEQ ID NO:11) (see Chaytor et al., in "Central role of heterocellular gap junctional communication in endothelium-dependent relaxations of rabbit arteries," *J. Physiol*. 508, 561(1998); Ko et al., in "Biochemical and functional characterization of intercellular adhesion and gap junctions in fibroblasts," *Am. J. Physiol. Cell Physiol*., 279, C147(2000); Richards et al., in "Suppression of K+-induced hyperpolarization by phenylephrine in rat mesenteric artery: relevance to studies of endothelium-derived hyperpolarizing factor," *Br. J. Pharmacol*., 134, 1(2001)).

Glycyrrhizinic acid (Glycyrrhizin), a saponin glycoside, is one of the compounds obtained from the root extract of licorice. This molecule has been well known for centuries, in traditional medicine, for its anti-inflammatory efficacy.

Ancient Greek physicians were the first to record that licorice helps coughs, colds, and asthmatic conditions. In Germany today, physicians still routinely recommend licorice in teas and syrups to control coughs.

The primary medicinal component in licorice root that helps asthma is glycyrrhetinic acid or glycyrrhizin.

Like the adrenal hormone cortisol, glycyrrhetinic acid acts as an anti-inflammatory in treating asthmatic and allergic reactions.

Glycyrrhetinic acid has the Molecular Formula $C_{30}H_{46}O_4$, a Molecular Weight of 470.64 and is represented by the following formula:

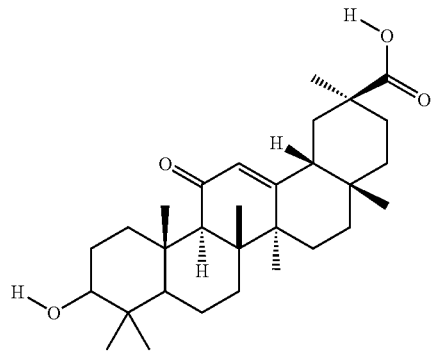

The herb source for glycyrrhetinic acid is the dry root and culm of licorice. Typically, glycyrrhetinic acid is available as an extract and can be obtained as a 98% pure material.

The term "isoform" in the context of the present invention refers to a "derivative" of a particular compound, including derivatives, such as, for example, esters and amides, of a carboxylic acid, including glycyrrhetinic acid, various protected forms thereof, and various compounds that can be converted thereto, such as, glycyrrhizinic acid and glycyrrhizin, which can be converted thereto in the liver or by hydrolysis.

Glycyrrhizin is changed in the liver to glycyrrhetinic acid. Both these compounds promote the activation of interferon, a potent, naturally produced antiviral compound. Once interferon is activated, white blood cells are also called into play along with killer T cells to help fight against the virus. This is how licorice exerts its effect on cold viruses, herpes simplex I and possibly HIV. Licorice also shows some antibacterial effects, but these are due more to the flavonoids than glycyrrhizin.

Upon hydrolysis, the glycoside is converted to the aglycone glycyrrhetinic acid. Glycyrrhizinic acid possesses antiviral properties. It has been reported to promote the activation of interferon and to inhibit the growth of several DNA and RNA viruses. It inactivates Herpes simplex virus particles irreversibly.

The antiviral activity of glycyrrhizinic acids is attributed to its ability to interact with the protein structure of the virus and interfere with its cycle. It inhibits the cytopathic growth and activity of the virus, thus preventing it from attacking healthy cells.

Glycyrrhizinic acid augments host resistance against *Candida albicans*, in subjects with thermal injuries. This is probably by inducing CD4 T cells, which suppress type 2 cytokines produced in burn associated injuries.

At a characteristic neuromuscular junction, a nerve impulse triggers the release of acetylcholine (AcH). AcH transmits an electrical signal that causes the muscle to contract. Excessive release of AcH causes hyperactive muscle contraction. Continuous or over stimulation of facial muscles due to hyperactivity increases signs of advanced aging (e.g., glabellar lines, crows feet and other deep wrinkles).

The choline transacetylation inhibitors are also suitable for use in the composition of the present invention.

The synthesis of AcH from AcetylCoA and choline is catalyzed by choline acetyl transferase. Inhibition of this pathway serves as a means to inhibit transmission of the electrical impulse and relax facial muscle contractions to reduce wrinkle formation.

The preferred choline transacetylation inhibitors include *stenolama chusana, portulaca oleracea, gynostemma pentaphyllum,* and *morinda citrifolia*. The choline acetyl transferase (CAT) inhibitors are present in the cosmetic compositions in a choline acetyl transferase inhibitory effective amount, and generally can be present in an amount up to about 50 wt % of the total weight of the composition.

Preferably, the choline acetyl transferase (CAT) inhibitor is at about 0.0001 wt % to about 20 wt % based on the total weight of the cosmetic composition. More preferably, the choline acetyl transferase (CAT) inhibitor is present at about 0.001 wt % to about 10 wt % based on the total weight of the cosmetic composition. Most preferably, the choline acetyl transferase (CAT) inhibitor is present at about 0.01 wt % to about 3 wt % based on the total weight of the cosmetic composition.

For use in the compositions of this invention, the various ingredients and/or active constituents can be in a pure form, a semi-pure form, or unpurified form. In a preferred embodiment, the components are in the form of an extract obtained by extraction with a suitable solvent, such as, an aqueous solvent and/or organic solvent.

*Stenoloma chusana* is a perennial herb found in Southeast Asia. Extracts from this plant are known to have uses in treating colds, influenza, bronchitis, burns, cuts, and skin sores (See A Barefoot Doctor's Manual, Running Press, Philadelphia, Pa., p. 638). The skin lightening uses thereof are described in the commonly owned U.S. Patent Publication No. 20040115146 A1, the contents of which are incorporated herein by reference.

Preferably, the *portulaca oleracea* is an extract derived from a purslane plant. Previously mentioned and commonly owned U.S. Patent Publication No. 20040126352 A1, the contents of which are incorporated herein by reference, describes the preparation of purslane plant extract prepared from the purslane plant according to methods known in the art (see, for instance, Example 1 therein).

Alternatively, "synthetic" extracts, i.e. various combinations of known Purslane plant components and/or constituents that are combined to substantially mimic the composition and/or activity of a Purslane plant extract of natural origin, can also be used.

The plant or natural extract can most preferably be derived from the *Portulaca oleracea* plant.

As stated above, the preferred components for use in the present invention are from the *Portulaca oleracea* plant. However, it is also contemplated that other members of the Purslane plant family would work equally as well including, but not limited to, *Portulaca sativa* and *Atriplex portulacoides*.

For use in the compositions of this invention, the Purslane plants or other components and/or active constituents are preferably derived directly from the plants.

The extract can further have one or more additional extracts, such as, *Portulaca sativa* extract, *Atriplex portulacoides* extract, and various combinations thereof.

*Gynostemma* is a member of the cucumber family. It is also known as 5-Leaf Ginseng, Jiaogulan and Southern Ginseng. The uses thereof to improve the aesthetic appearance of skin, hair and nails, are described in the commonly owned U.S. Patent Publication No. 20030124205 A1, the contents of which are incorporated herein by reference.

*Gynostemma* has traditionally been grown in the mountainous regions of South Central China. This herb is a different plant from what is commonly known as ginseng. It is a rich source of saponins referred to as "gypenosides", which are similar, and in some cases identical, to the ginsenosides found in ginseng, but are found at levels several fold higher than those found in ginseng. These saponins have been shown to have antioxidant or cell protective effects. *Gynostemma* (Jiaogulan) can be purchased as a powder form.

In cosmetic compositions of the present invention, *gynostemma pentaphyllum* is preferred.

Extracts of *Morinda citrifolia* are derived from the Indian Mulberry plant. *Morinda citrifolia* has been used in compositions for reducing oxysterol buildup in the blood and normalizing cholesterol and blood pressure in mammals as set forth in U.S. Pat. No. 6,387,370 to Yegorova. A method of extracting and purifying an essential oil product of *Morinda citrifolia* is disclosed in U.S. Pat. No. 6,417,157 to Wadsworth et al. The skin lightening uses of *Morinda citrifolia* are described in the previously incorporated and commonly owned U.S. Patent Publication No. 20040115146 A1.

Preferably, the plant extracts set forth above are present in an amount from about 0.0001 wt % to about 20 wt %, based upon the total weight of the composition. More preferably, the extracts are is present in an amount from about 0.001 wt % to about 10 wt %, based upon the total weight of the composition. Most preferably, the extracts are present in an amount from about 0.01 wt % to about 3.0 wt %, based upon the total weight of the composition.

The cosmetic composition can have one or more gap junction inhibitors, such as, Gap 27 peptides, glycyrrhetinic acid, and isoforms of glycyrrhetinic acid present in the composition in a gap junction inhibitory effective amount. Preferably, the total amount of the gap junction inhibitors is up to about 50 wt % of the total weight of the composition. More preferably, the gap junction inhibitor is at about 0.0001 wt % to about 40 wt % based on the total weight of the cosmetic composition. Most preferably, the gap junction inhibitor is present at about 0.1 wt % to about 10 wt % based on the total weight of the cosmetic composition.

Preferably, the gap junction inhibitors have a Gap 27 peptide, which is present in an amount from about 0.0001 wt % to about 10 wt %, based upon the total weight of the composition.

The gap junction inhibitor can be glycyrrhetinic acid and/or one or more isoforms of glycyrrhetinic acid. Preferably, glycyrrhetinic acid an/or the isoforms of glycyrrhetinic acid are present in an amount from about 0.0001 wt % to about 10 wt %, based upon the total weight of the composition.

In a preferred embodiment, the cosmetic composition according to the present invention can have both of: (1) one or more choline transacetylation inhibitors; and (2) one or more gap junction inhibitors. In this case, the total amount of one or more choline acetyl transferase (CAT) inhibitors and one or more gap junction inhibitors is up to about 50 wt % of the total weight of the composition.

Gap junctions mediate electrical and chemical coupling between cells. They are constructed from transmembrane proteins called connexins, which form aqueous channels between two cells.

Without being bound by any theory or structure, it is believed that the inhibitory Gap 27 peptide, containing sequence homology with one of these channel proteins, acts by inducing conformational changes and the glycyrrhetinic acid and/or the isoforms of glycyrrhetinic acid alter the phosphorylation state of connexins. These changes can cause disruption of cell-cell communication, which inhibit transmission of an electrical impulse between cells. The perturbation caused by these changes results in the closing of the channel and relaxation of the muscle. Accordingly, it is believed that such relaxation of the facial skeletal muscles reduces the appearance of deep wrinkles.

It is generally accepted that the rate-limiting step in the synthesis of AcH in nervous tissue is the availability of choline for conversion. Some methods have focused on separate pathways, such as, increased destruction of AcH and inhibition of AcH secretion, to achieve similar endpoints, i.e., reduction of glabellar lines and deep wrinkles.

In nervous tissue, activity of high-affinity choline transport system controls the uptake of choline into the cell. However, in the placenta, the rate-limiting step for AcH synthesis is the activity of CAT that catalyzes acetyl-CoA and choline into AcH.

Unlike the nervous system, cells that have the placenta, as is the case in facial skin, are composed of epithelial cells. If synthesis of AcH in the skin is regulated like the placenta, the inhibition of the transacetylation of choline catalyzed by choline acetyl transferase can decrease the rate of synthesis and levels of AcH in the skin resulting in the relaxation of facial muscles.

Inhibition of cell-cell communication using gap junctions as a means by which to relax facial skeletal muscles has not been described or addressed in the scientific literature. Accordingly, the present invention provides a cosmetic composition that has a cosmetically acceptable vehicle and an effective amount of one or more of Gap 27 peptides, glycyrrhetinic acid, an isoform of glycyrrhetinic acid, *stenolama chusana, portulaca oleracea, gynostemma pentaphyllum, morinda citrifolia*, and any combinations thereof.

The cosmetic composition can be organic solvent based, water based or it can be an emulsion. Such organic solvent, water, or emulsion-based compositions are known in the art and therefore, are not discussed further herein.

The cosmetic compositions have a cosmetically acceptable vehicle and contain an effective amount of one or more of the gap junction inhibitors and/or choline acetyl transferase (CAT) inhibitors according to the present invention.

The cosmetic composition can further have one or more additional "cosmetically active ingredients" such as, protective agents, anesthetics, anti-allergenics, antifungals, antimicrobials, anti-inflammatory agents, antiseptics, exfolients, pharmaceuticals, film formers, sunscreens, skin penetration enhancers, or any combinations thereof.

Preferably, the cosmetically active ingredient is present at about 0.001 wt % to about 10 wt % based on the total weight of the cosmetic composition.

Preferably, the cosmetically active ingredient can be, but is not limited to, one or more of the following: anesthetics, anti-allergenics, antifungals, antimicrobials, anti-inflammatory agents, antiseptics, exfolients, pharmaceuticals, film formers, sunscreens, and skin penetration enhancers, any derivatives thereof, or any combinations thereof.

Preferably, the sunscreen is one or more of the following: dibenzoylmethane, oxybenzone, sulisobenzone, dioxybenzone, menthyl anthranilate, para aminobenzoic acid ester, benzophone-3, butyldibenzoylmethane, dimethyl cinnamate, octyl methoxycinnamate, DEA methoxycinnamate, octocrylene, drometrizole trisiloxane, octyl salicylate, homomethyl salicylate, octyl dimethyl PABA, TEA salicylate, 4-methyl benzilidene camphor, 3-benzylidene camphor, benzylidene camphor sulfonic acid ester, octyl triazone, phenyl benzimidazole sulfonic acid ester, terephthalydiene dicamphor sulfonic acid ester, di-t-butyl hydroxybenzylidene camphor, ethyl PABA, butylmethoxy dibenzoylmethane, terephthalydiene methylene bis-benzotriazoyltetramethylbutyl-phenol, diethylhexyl-2,6-naphthalate, bis-ethylhexyloxyphenol methoxyphenol triazine, hydroxy methylphenyl benzotriazole, methylene bis-benzotriazoyltetramethylbutylphenol, bis-ethylhexyloxyphenol methoxyphenol triazine, hydroxybenzophenone, a benzotriazole, a dibenzoyl methane, an oxanilide, a hydroxy cinnamate, oil dispersible titanium dioxide, oil dispersible zinc oxide, a silicone-anchored sunscreen, para aminobenzoic acid, salicylic acid, TEA salicylate, benzylidene camphor sulfonic acid, phenyl benzimidazole sulfonic acid, terephthalydiene dicamphor sulfonic acid, hydroxy cinnamic acid, any derivatives thereof, or any combinations thereof.

Examples of the suitable additives include:

antioxidants, such as, rosemary extract, tocopherol, a derivative of tocopherol including a tocotriene, carotene, a carotenoid, a phenolic antioxidant including a phenolic acid, a bioflavonoid, a plant extract, curcumin, tetrahydrocurcumin, camphorol, quercetine, epigenine, and any mixtures thereof.

The preferred antioxidants are tocopherols and bioflavonoid that have demonstrated antioxidant activity, including *ginkgo biloba*, pyconogyl pycoogeonyl, pycyogenol, genistein, daidzein, and any combinations thereof;

keratolytic agents, such as, salicylic acid, resorcinol, peroxide of an organic acid, and any combinations thereof;

anti-inflammatory agents, such as, steroidal and non-steroidal anti-inflammatory agents and plant extracts that have demonstrated anti-inflammatory activity;

vitamins, such as, Vitamin K, retinol (vitamin A), tocopherol, and any combinations thereof;

emollients, such as, cetearyl octanoate, octyl palmitate, butylene glycol, propylene glycol, glycerine, glyceryl monostearate, petrolatum, caprylic trigylceride, capric trigylceride, shea butter, silicone oil, and any combinations thereof;

humectants, such as, glycerin, propylene glycol, butylene glycol, hyaluronic acid, one or more derivatives of hyaluronic acid, and any combinations thereof;

skin penetration enhancers, such as, ozone, SEPA, butylene glycol, cis-isomer of an unsaturated fatty acid, and any combinations thereof;

emulsifiers, such as, glyceryl stearate, cetearyl alcohol, cetyl alcohol, PEG-40 stearate, and any combinations thereof;

thickening agents, such as, xanthan gum, carbomer, clay, hydroxyethyl cellulose, and any combinations thereof;

film formers, such as, trimethyl siloxysilicate, nitrocellulose, cellulose acetate butyrate, alkyd resins, polyester resins, acrylic resins, low molecular weight polyurethane resins, polyamide resins, vinyl resins, arylsulfonamide aldehyde resins, arylsulfonamide epoxy resins, and any combinations thereof;

retinoids, such as, retinol, one or more esters of retinol, retinoic acid, one or more esters of retinoic acid, a compound that can mimic retinol, and any combinations thereof;

preservatives, such as, an alkyl paraben, an alcohol, imidazolidinyl urea, and any combinations thereof;

colorants, such as, synthetic and natural colorants;

chelating agents, such as, disodium EDTA; and pH adjusters, such as, an acid, a base, or a buffer, to adjust and maintain the pH to about 6.5 to about 7.5.

Other additives include one or more of proteins, colorants, pigments, including photo-chromic and thermo-chromic colorants and pigments, and other appropriate materials suitable for use in cosmetic applications.

The present cosmetic compositions typically have a vehicle. The vehicle should be a cosmetically acceptable or suitable vehicle. In the context of the present invention, the term "cosmetically acceptable vehicle" or "suitable vehicle" refer to any vehicle for a drug, a cosmetic or a medicament that is suitable for use in direct, safe contact with human tissues.

The vehicle of the cosmetic composition is preferably suitable for use in applications that require direct contact with human tissue. The tissue is preferably skin. The vehicle can be a solid, a fluid, emulsion, balm, an aerosol or a pump spray.

The solid vehicle is preferably a patch, a tape, or a powder. The fluid vehicle is preferably a liquid, a lotion, or a gel.

The cosmetic composition is preferably a product, such as, cosmetic composition is in the form of a product selected from body wash, bar soap, liquid soap, skin care preparation, lipstick, mascara, color cosmetic, foam, mousse, solution, emulsion, cream, lotion, pomade, balm, stick, gel, pump spray, aerosol spray, a targeted delivery system, a mask, a transdermal patch, or any combinations thereof.

More preferably, the cosmetic product is a skin care preparation in the form of a cream, lotion or pomade.

The present invention further provides a method of reducing the appearance of deep wrinkles on skin, preferably on human skin.

The method includes the step of topically applying to the skin a cosmetic composition having a cosmetically acceptable vehicle; and an effective amount of one or more of a gap junction inhibitors and/or one or more of choline acetyl transferase (CAT) inhibitors in an amount effective to reduce the appearance of deep wrinkles on the skin.

Preferably, the composition is applied once, twice or more than twice daily, preferably once daily. Preferably, the composition is applied for a period of time sufficient to reduce the appearance of deep wrinkles on the skin, such as, facial skin, including particularly "crows feet" lines by the eyes and deep lines above the upper lip and the sides of the mouth. Typically, the period of time sufficient to reduce the appearance of deep wrinkles is at least one week, especially at least two weeks, and even more especially the period of time is three or more weeks.

The reduction in the appearance of deep wrinkles on the skin is manifested by a decrease in the number of hyperkinetic facial lines, wrinkles, creases or folds and/or a decrease in the depth thereof.

The cosmetic composition according to the present invention has utility in cosmetic and personal care preparations by providing a cosmetic composition for and a method of reducing the appearance of deep wrinkles on skin, preferably on human skin.

The procedures that follow are illustrative of the various aspects present invention. They should not be construed as being limiting in any manner.

General Method Choline Acetyltransferase Assay:

This procedure measures the activity of choline acetyltransferase (ChAT) in brain tissue in vitro. The assay is based on the formation of $^{14}C$ acetylcholine from $^{14}C$ acetyl coenzyme A and choline. The product is isolated by column chromatography using Dowex AG 1×8 (400 mesh). Reference: Ball and Oderfeld-Nowak, J. Neurochemistry, 18, 935-947 (1971).

EXAMPLE 1

TABLE 1 summarizes the results obtained in an in vitro measurement of the activity of choline acetyltransferase (CHAT) in brain tissue.

TABLE 1

| Choline Acetyltranferase Enzyme Activity | |
| --- | --- |
| Compound (1.0% w\v) | Percent Inhibition |
| portulaca oleracea | 72.89 |
| stenolama chusana | 70.07 |
| gynostemma pentaphyllum | 37.66 |
| morinda citrifolia | 30.67 |

EXAMPLE 2

Procedure for Preparation of Plant Extracts: The plant extracts are prepared by an organic solvent extraction method, which includes washing and extracting a plant material typically with an organic solvent. Non-limiting examples of organic solvents include methanol, ethanol, isopropanol, dichloromethane, chloroform, hexane, xylene, and petroleum ether. An extracting machine may be used for organic solvent extraction as is well known in the field.

Organic solvent extraction includes the step of collecting the raw materials from the plant that contain the desired constituent(s), such as seeds, needles, leaves, roots, bark, cones, stems, rhizomes, callus cells, protoplasts, organs and organ systems, and meristems. Thereafter, the plant material is ground to small particle size, and put into an extracting machine through an inlet for the raw materials by a measurable charging machine.

The plant raw material is pushed in the extracting machine by a thruster, which slowly moves the plant raw material forward. An organic solvent, e.g., ethanol, may be added into the machine through a solvent inlet at the top of a waste discharge outlet. Due to the difference in gravity and equilibrium, the solvent flows toward the raw material inlet, soaks the materials and flows out from the opposite side of the solvent inlet.

Since the plant materials and the solvent move in opposite directions against each other, the plant materials are constantly immersed in a solution that contains a low-concentration of extract. As a result of equilibrium, high yield of plant constituent(s) may be achieved by continuously extracting the plant material against the low-concentration solution.

An extraction time suitable to extract the plant constituents is used, typically between about 1 to about 8 hours is suitable, more preferably between about 2 to 6 hours, and most preferably between about 3 to about 5 hours. Typically, the temperature of extraction is between about 30° C. to about 90° C., preferably between about 40° C. to about 70° C., and more preferably between about 50° C. to about 60° C.

The collected extract is then fine-filtered to remove debris, and may be used directly, or is concentrated, for example by distilling the solvent or by other conventional processing. A typical extract actives content is about 25 wt % or more, preferably 50 wt % or more. The extract can also be provided as a residue after evaporation of the solvent, either in powder form or as a thick oily residue. Aqueous ethanol (80/20 ethanol/water) is preferred.

The aqueous-organic solvent extraction also includes the step of initially collecting raw materials from a plant containing the desired constituents, such as seeds, needles, leaves, roots, bark, cones, stems, rhizomes, callus cells, protoplasts, organs and organ systems, and meristems of the plant, which are ground into small particle sizes. The ground plant material is soaked in aqueous solution that is acidic or alkaline, depending on the solubility and stability of the desired extract under acidic or alkaline (basic) conditions.

For extraction under acidic conditions, an acid such as hydrochloric acid or sulfuric acid is added to water, e.g., at a concentration of about 3% weight by volume (w/v). For extraction under alkaline conditions, an alkali such as sodium hydroxide or sodium carbonate is added to water.

The extraction time and temperature of extraction are typically similar to that used in the organic solvent extraction method described above.

The extract is then collected and fine-filtered to remove debris. Alkaline agents, e.g., ammonia, or acidifying agents, e.g., sulfuric acid, may be added to the extract to neutralize the solution by adjusting the pH, depending on the acidity or alkalinity of the collected extract.

The aqueous extract may be used directly, concentrated or dried. Alternatively, organic solvent may then be added to the neutralized solution to transfer the extract from an aqueous phase to an organic phase.

Examples of such organic solvents include, but are not limited to, ethanol, isopropanol, butanol, pentanol, hexanol, xylene, and any combinations thereof. The extract having the transferred extract actives dissolved in organic solvent may be used directly, used as a concentrate, or dried.

In a mixed extraction approach, different plants containing different constituents may be mixed and extracted together. This process of mixed extraction may preferably be used for extracting plants that contain constituents having similar solubility in the solvent used for extraction, such as ethanol. Thereafter, the mixture of extracts may be concentrated as before and stored in an appropriate solvent.

It should be understood that the foregoing description is only illustrative of the present invention. Various alternatives and modifications can be devised by those skilled in the art without departing from the present invention. Accordingly, the present invention is intended to embrace all such alternatives, modifications and variations that fall within the scope of the appended claims.

---

---

What is claimed is:

1. A method of reducing the appearance of wrinkles on skin of a person in need thereof, comprising: topically applying to wrinkles a composition comprising a cosmetically acceptable vehicle and an effective amount of:
   (i) one or more of gap junction inhibitors selected from Gap 27 peptides, and
   (ii) one or more of choline acetyl transferase (CAT) inhibitors selected from the group consisting of plant extracts of *stenolama chusana, portulaca oleracea, gynostemma pentaphyllum*, and *morinda citrifolia*,
wherein the total amount of said one or more gap junction inhibitors and said one or more choline acetyl transferase (CAT) inhibitors is between about 0.0001 wt % and about 50 wt % of the total weight of the composition and wherein said composition is applied in an amount and for a period of time sufficient to reduce the appearance of wrinkles on the skin.

2. The method of claim 1, wherein said composition is applied at least once daily for a period of at least one week.

3. The method of claim 2, wherein the skin is facial skin.

4. The method of claim 1, wherein the reduction in the appearance of wrinkles on the skin is manifested by a decrease in the number of hyperkinetic facial lines, wrinkles, creases or folds and/or a decrease in the depth thereof.

5. The method of claim 1, wherein said choline acetyl transferase inhibitor is present in a total amount of about 0.001 wt % to about 10 wt % of the total weight of the composition and wherein said gap junction inhibitors are present in a total amount of about 0.001 wt % to about 10 wt % of the total weight of the composition.

6. The method of claim 1, wherein: up to about 25 wt %, based on the total weight of the cosmetic composition, is comprised of a cosmetically active ingredient of one or more anesthetics, anti-allergenics, antifungals, antimicrobials, anti-inflammatory agents, antiseptics, exfollients, pharmaceuticals, film formers, sunscreens, skin penetration enhancers, or any combinations thereof.

7. The method of claim 1, wherein the cosmetic composition is in the form of a product selected from the group consisting of body wash, bar soap, liquid soap, skin care preparation, lipstick, mascara, color cosmetic, foam, mousse, solution, emulsion, cream, lotion, pomade, balm, stick, gel, pump spray, aerosol spray, a targeted delivery system, a mask, a transdermal patch, and any combinations thereof.

8. The method of claim 1, wherein said one or more of choline acetyl transferase (CAT) inhibitors are selected from the group consisting of plant extracts of *stenolama chusana*, *gynostemma pentaphyllum*, and *morinda citrifolia*.

\* \* \* \* \*

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial
<220> FEATURE:
<223> OTHER INFORMATION: The synthetic Gap 27 peptide is derived from
      Connexin 43.

<400> SEQUENCE: 1

Ser Arg Pro Thr Glu Lys Thr Ile Phe Ile Ile
1               5                   10
```